(12) United States Patent
Tanaka et al.

(10) Patent No.: US 8,529,534 B2
(45) Date of Patent: Sep. 10, 2013

(54) EXCREMENT TREATING APPARATUS

(75) Inventors: Tetsuya Tanaka, Tokyo (JP); Yoshikazu Ishitsuka, Omitama (JP); Ryosuke Miyagawa, Kasukabe (JP); Ichiro Wada, Kanonji (JP); Miou Suzuki, Kanonji (JP)

(73) Assignees: Hitachi, Ltd., Tokyo (JP); Uni-Charm Corporation, Ehime (JP)

( * ) Notice: Subject to any disclaimer, the term of this patent is extended or adjusted under 35 U.S.C. 154(b) by 313 days.

(21) Appl. No.: 12/865,871

(22) PCT Filed: Jan. 6, 2009

(86) PCT No.: PCT/JP2009/000006
§ 371 (c)(1),
(2), (4) Date: Aug. 20, 2010

(87) PCT Pub. No.: WO2009/122629
PCT Pub. Date: Oct. 8, 2009

(65) Prior Publication Data
US 2011/0009840 A1 Jan. 13, 2011

(30) Foreign Application Priority Data
Mar. 31, 2008 (JP) .................................. 2008-089697

(51) Int. Cl.
*A61F 5/44* (2006.01)
(52) U.S. Cl.
USPC ........... 604/338; 604/361; 604/327; 340/604; 340/605; 340/620; 600/300; 600/301; 128/917; 128/912; 324/694
(58) Field of Classification Search
USPC ................................. 604/361, 327
See application file for complete search history.

(56) References Cited

U.S. PATENT DOCUMENTS

| 7,221,279 | B2 | 5/2007 | Nielsen |
| 8,046,848 | B2 * | 11/2011 | Birbara et al. ................. 4/144.1 |
| 8,115,643 | B2 | 2/2012 | Wada et al. |

FOREIGN PATENT DOCUMENTS

| JP | 54-127391 | A | 10/1979 |
| JP | 9-196875 | A | 7/1997 |
| JP | 2000-93448 | A | 4/2000 |
| JP | 2004-529730 | A | 9/2004 |
| JP | 2005-13244 | A | 1/2005 |
| JP | 2005-102979 | A | 4/2005 |
| JP | 2006-26108 | A | 2/2006 |
| JP | 2007-44494 | A | 2/2007 |
| JP | 2008-8791 | A | 1/2008 |
| JP | 2008-043501 | A | 2/2008 |
| WO | 2008/001475 | A1 | 1/2008 |

* cited by examiner

*Primary Examiner* — Tatyana Zalukaeva
*Assistant Examiner* — Ilya Treyger
(74) *Attorney, Agent, or Firm* — Mattingly & Malur, PC

(57) ABSTRACT

An excrement treating apparatus 100 includes an excretion receiver 1 and an apparatus body 2. The excretion receiver 1 includes a receiver body 10 which receives excretions and an excretion sensor 20 which detects the excretions. The apparatus body 2 includes a urine tank 51 which stores urine, a vacuum pump 52 which sucks urine received by the receiver body 10 into the urine tank 51, and a control unit 53. The excretion sensor 20 includes a pair of urine sensor electrodes 21 and 22 which detect urine received by the receiver body 10. The control unit 52 controls so as to reverse the polarity of the urine sensor electrodes 21 and 22 at prescribed time intervals. In the excrement treating apparatus, the excretion sensor's sensitivity is stabilized and urination is accurately detected and treated.

3 Claims, 7 Drawing Sheets

EXCREMENT TREATING APPARATUS

TECHNICAL FIELD

The present invention relates to an excrement treating apparatus and more particularly to an excrement treating apparatus which treats excretions with a person wearing an excretion receiver with a sensor to detect excretion.

BACKGROUND ART

Excrement treating apparatuses which treat excretions with a person with difficulty in walking, a hospitalized patient or a physically handicapped person wearing an excretion receiver have been developed.

One example of a conventional excrement treating apparatus is disclosed in JP-A No. 2005-102979 (Patent Document 1).

The excrement treating apparatus described in Patent Document 1 includes: a urine receiver to be worn by a person; a urine tank to store urine, a urine guide tube which guides urine from the urine receiver into the urine tank; a vacuum pump which sucks in urine from the urine receiver through the urine guide tube and stores urine into the urine tank; and a control unit which controls the vacuum pump.

The urine receiver has a urine anti-backflow sheet with funnel-shaped holes between a surface sheet and a urine absorption sheet and a urine sensor between the surface sheet and urine anti-backflow sheet. The urine sensor includes a pair of electrodes which are bonded to an electrode support sheet in parallel with each other with signal lines connected with the electrodes. The signal lines are connected with the control unit.

In the excrement treating apparatus described in Patent Document 1, when urine is accumulated between the pair of electrodes, urination is detected by electricity flowing between the conductive surfaces of the paired electrodes. The urine detection signal is sent to the control unit through a signal line and the control unit activates the vacuum pump. As the vacuum pump is activated, the air pressure in the urine tank goes down, generating a negative pressure at a urine guide hole of the urine receiver and urine is sucked into the urine guide tube by an absorption force due to this negative pressure so that urine is guided into the urine tank and stored there.

Also, another conventional excrement treating apparatus is disclosed, for example, in JP-A No. 2008-8791 (Patent Document 2).

The excrement treating apparatus described in Patent Document 2 includes a excretion receiver to be worn by a person; a urine tank to store urine, a tube which guides urine from a tray provided in the excretion receiver into the tank; a vacuum pump which sucks in urine from the excretion receiver through the tube and stores urine in the tank; and a control unit which controls the vacuum pump.

An excretion sensor provided in the excretion receiver includes two pairs of lead wires (electrodes) which extend in parallel with each other and are inserted between a support and a covering, both waterproof and insulating. The excretion sensor is inserted between various lamination sheets of the excretion receiver. Urine guide holes of the excretion sensor are provided in the urine receiving portion of the excretion receiver and feces guide holes of the excretion sensor are provided in its feces receiving portion. A tray for receiving urine is located below the excretion sensor in the urine receiving portion of the excretion receiver. This tray is connected with the vacuum pump through the tube.

In the excrement treating apparatus described in Patent Document 2, when a person wearing the excretion receiver discharges urine, the urine soaks into the urine receiving portion of the excretion receiver, further flows toward the excretion sensor side, touches the surface of the excretion sensor, and gets into a urine guide hole, causing short-circuiting between one pair of lead wires. As a consequence, a signal for notification of urination is sent from the excretion sensor to the control unit and upon receipt of this signal, the control unit activates the vacuum pump to convey the urine from the tray to the tank.

When the person wearing the excretion receiver defecates, the moisture of the feces soaks into the urine receiving portion of the excretion receiver and flows toward the excretion sensor side, touches the surface of the excretion sensor, and gets into a feces guide hole, causing short-circuiting between the other pair of lead wires. As a consequence, a signal for notification of defecation is sent from the excretion sensor to the control unit and the control unit activates a warning device to notify of defecation.

[Patent Document 1] JP-A No. 2005-102979
[Patent Document 2] JP-A No. 2008-8791

DISCLOSURE OF THE INVENTION

Problem to be Solved by the Invention

The excrement treating apparatus described in Patent Document 1 has a problem that due to accumulation of impurities in urine on the conductive surfaces of a pair of electrodes, the sensitivity of the urine sensor deteriorates and upon urination the urine sensor fails to detect it immediately, causing a urination treatment failure. The excrement treating apparatus described in Patent Document 1 does not disclose detection of excreted feces.

On the other hand, in the excrement treating apparatus described in Patent Document 2, due to accumulation of impurities in urine or feces moisture on the conductive surfaces of two pairs of lead wires, the sensitivity of the excretion sensor deteriorates and upon urination or defecation, the excretion sensor fails to detect it, causing an excretion treatment failure.

Furthermore, the excrement treating apparatus described in Patent Document 2 has also a problem that if the excreted urine gets into both a urine guide hole and a feces guide hole and adheres to both a urine detection conductor and a feces detection conductor or excreted feces gets into both a urine guide hole and a feces guide hole and adheres to both a urine detection conductor and a feces detection conductor, urine and feces cannot be detected in a discriminative manner.

An object of the present invention is to provide an excrement treating apparatus which ensures stability in the sensitivity of an excretion sensor and detects urination immediately and accurately and performs urine treatment.

Another object of the present invention is to provide an excrement treating apparatus which discriminates between urination and defecation accurately and performs excretion treatment.

Means for Solving the Problem

In order to achieve the above objects, according to a first aspect of the present invention, an excrement treating apparatus includes an excretion receiver to be worn by a person, and an apparatus body detachably connected with the excretion receiver, where the excretion receiver includes a receiver body which receives excretions discharged from a wearer and an excretion sensor which detects the excretions, and the apparatus body includes a urine tank which stores urine, a vacuum pump which sucks urine received by the receiver body into the urine tank, and a control unit which controls the vacuum pump, and the excretion sensor includes at least one pair of urine sensor electrodes which detect urine received by the receiver body; and the control unit controls so as to reverse the polarity of the urine sensor electrodes at prescribed time intervals.

Preferred embodiments according to the first aspect of the present invention are as follows.

(1) The urine sensor electrodes are inserted between a waterproof insulating band-like support and a waterproof insulating band-like covering, extending in parallel with each other like bands; the covering has at least one pair of urine guides correlated with the urine sensor electrodes; and the excretion sensor detects urination when urine received by the receiver body enters the pair of urine guides and causes short-circuiting between the urine sensor electrodes.

(2) The apparatus body includes a DC power supply and a connector connected with electric wires extending from the DC power supply and the urine sensor electrodes are connected with the DC power supply through the connector and the electric wires.

(3) In addition to the above (2), the apparatus body includes a polarity reversal circuit which reverses polarity of the electric wires and the control unit reverses polarity of the urine sensor electrodes by controlling the polarity reversal circuit so as to reverse the polarity of the electric wires.

(4) In addition to the above (2), the apparatus body includes detection means for detecting resistance between the electric wires and the control unit controls the vacuum pump according to a result of detection by the detection means.

(5) The excretion sensor includes a pair of feces sensor electrodes which detect feces received by the receiver body.

(6) In addition to the above (5), the control unit controls so as to reverse the polarity of the feces sensor electrodes at prescribed time intervals.

(7) In addition to the above (5), the control unit controls so as to perform switching between urine detection by the urine sensor electrodes and feces detection by the feces sensor electrodes.

(8) In addition to the above (6), the control unit controls so as to alternately perform switching between urine detection by the urine sensor electrodes and feces detection by the feces sensor electrodes and switching between polarity reversal of the urine sensor electrodes and polarity reversal of the feces sensor electrodes.

(9) In addition to the above (6), a prescribed time interval for polarity reversal of the urine sensor electrodes and the feces sensor electrodes is within a range from 0.1 to 1 second.

(10) In addition to the above (5), voltage to be applied between the urine sensor electrodes or between the feces sensor electrodes is within a range from 1 to 10 V.

In order to achieve the above objects, according to a second aspect of the present invention, an excrement treating apparatus includes an excretion receiver to be worn by a person and an apparatus body detachably connected with the excretion receiver, where the excretion receiver includes a receiver body which receives excretions discharged from a wearer and an excretion sensor which detects the excretions, the apparatus body includes a urine tank which stores urine, a vacuum pump which sucks urine received by the receiver body into the urine tank and a control unit which controls the vacuum pump, the excretion sensor includes a pair of urine sensor electrodes which detect urine received by the receiver body, and the control unit controls so as to apply voltage between the urine sensor electrodes intermittently.

In order to achieve the above objects, according to a third aspect of the present invention, an excrement treating apparatus includes an excretion receiver to be worn by a person; and an apparatus body detachably connected with the excretion receiver, where the excretion receiver includes a receiver body which receives excretions discharged from a wearer and an excretion sensor which detects the excretions, the apparatus body includes a urine tank which stores urine, a vacuum pump which sucks urine received by the receiver body into the urine tank and a control unit which controls the vacuum pump, the excretion sensor includes a pair of urine sensor electrodes which detect urine received by the receiver body and a pair of feces sensor electrodes which detect feces received by the receiver body, and the control unit controls so as to perform switching between detection by the urine sensor electrodes and detection by the feces sensor electrodes.

EFFECT OF THE INVENTION

In the excrement treating apparatus according to the first aspect of the present invention, the sensitivity of the excretion sensor is stabilized and urination can be accurately detected and treated.

In the excrement treating apparatus according to the second aspect of the present invention, the sensitivity of the excretion sensor is stabilized and urination can be accurately detected and treated.

In the excrement treating apparatus according to the third aspect of the present invention, urination and defecation can be accurately distinguished and treated.

BEST MODE FOR CARRYING OUT THE INVENTION

Next, an embodiment of the present invention will be described referring to FIGS. 1 to 8.

As shown in FIG. 1, an excrement treating apparatus 100 includes an excretion receiver 1 and an apparatus body 2. The excretion receiver 1 and apparatus body 2 are connected through a urine guide tube 30, electric wires 61, 62, and a connector 42 in a disconnectable manner. FIG. 1 shows the general structure of the excrement treating apparatus 100 according to this embodiment.

As shown in FIGS. 1 and 2, the excretion receiver 1 includes a receiver body 10 which is designed to be worn by a person with difficulty in walking, a hospitalized patient or a physically handicapped person between his or her legs and receive urine or feces excreted by the wearer; an excretion sensor 20 which detects excreted urine and feces; and a urine guide tube 30 which guides excreted urine from the receiver body 10 into a urine tank 51. This excretion receiver 1 is made of a flexible material. FIG. 2 is an enlarged sectional view of the excretion receiver 1 shown in FIG. 1 and for easy understanding, various members are illustrated as if they were separate from each other but actually they are united.

Urine guides 28 in the excretion sensor 20 are provided in the receiver body 10's urine receiving portion 10a and feces guides 29 in the excretion sensor 20 are provided in its feces receiving portion 10b. The excretion sensor 20 is used as inserted between lamination sheets of the receiver body 10. A urine tray 13 is provided under the excretion sensor 20 in the urine receiving portion 10a of the receiver body 10. The urine tray 13 is connected with the urine tank 51 through the urine tube 30. Urine in the urine tray 13 is conveyed into the urine tank 51 by suction of a vacuum pump 52. Alternatively, the excretion sensor 20 may have a plurality of urine guides 28 and a plurality of feces guides 29 arranged alternately. In that case, urine and feces can be detected more accurately.

As shown in FIG. 2, the receiver body 10 includes a back sheet 12, a urine tray 13, a surface material member 14, a surface sheet 15, and a gathering 16 in a way that they are stacked from the bottom in the order of mention.

The urine tray 13 includes a liquid-permeable sheet 13a, a leak-proof sheet 13b placed on the wearer side of the liquid-permeable sheet 13a, and spacers 13c placed in the space between the liquid-permeable sheet 13a and the leak-proof sheet 13b. The space between the liquid-permeable sheet 13a and the leak-proof sheet 13b is a closed space and connected with the urine guide tube 30 in a communicable manner. The spacers 13c are spherical and retain the spacing between the liquid-permeable sheet 13a and the leak-proof sheet 13b.

The surface material member 14 is provided on the non-wearer side of the liquid-permeable sheet 13a to receive urine excreted by the wearer temporarily. The surface sheet 15 covers the wearer side surface of the liquid-permeable sheet 13a.

The back sheet 12 covers the non-wearer side surface of the leak-proof sheet 13b to prevent urine from leaking form the urine tray 13. The surface sheet 15 and back sheet 12 have a gourd-like shape and are bonded to each other, with their rims sticking fast to each other.

As shown in FIGS. 3 to 5, in the excretion sensor 20, two pairs of electrodes 21, 22, 23, and 24, extending in parallel with each other, are inserted between a waterproof insulating band-like support 26 and a waterproof insulating band-like covering 27. FIG. 3 is a plan view showing the excretion sensor 20 as divided in halves; FIG. 4 is a sectional view taken along the line A-A in FIG. 3; and FIG. 5 is a sectional view taken along the line B-B in FIG. 3.

In the covering 27, at least one pair of urine guides 28 to correlate one pair of electrodes 21 and 22 are formed and a pair of urine guides 29 to correlate the other pair of electrodes 23 and 24 are formed. In the example shown in the figures, the urine guides 28 and feces guides 29 are rectangular holes; however, alternatively they may be notches made in the rims at both sides of the covering 27. As urine A enters a correlated urine guide 28, short-circuiting occurs between the one pair of electrodes 21 and 22 as shown in FIG. 4. As feces B enters a correlated feces guide 29, short-circuiting occurs between the other pair of electrodes 23 and 24 as shown in FIG. 5.

The support 26, which supports the entire excretion sensor 20, is a flexible band-like piece. The support 26 has water-tightness to prevent moisture penetration and has an insulating property to prevent electrical conduction.

The two pairs of electrodes 21, 22, 23 and 24 extend in parallel with each other along both edges of the band-like piece or support 26. Among them, the inner pair of electrodes 21 and 22 are used to detect urination and the outer pair of electrodes 23 and 24 are used to detect defecation. Relatively large terminals 21a, 22a, 23a and 24a are formed at the base ends of the two pairs of electrodes 21, 22, 23, and 24 where a connector 42 is connected. Extensions 23b and 24b are formed at the non-terminal side ends of the feces sensor electrodes 23 and 24. While the extensions 23b and 24b as the ends of the feces sensor electrodes 23 and 24 are provided at an end of the support 26, the urine sensor electrodes 21 and 22 terminate at a point nearer to the base ends than the extensions 3b and 4b of the feces sensor electrodes 23 and 24. In other words, ends of the urine sensor electrodes 21 and 22 and their vicinities, and the extensions 23b and 24b of the feces sensor electrodes 23 and 24 are located so as to correspond to the urine receiving portion 10a and the feces receiving portion 10b respectively.

The covering 27 lies over the electrodes 21, 22, 23 and 24, covering almost the entire surface of the support 26 except the terminals 21a, 22a, 23a, and 24a and the guides 28 and 89. The covering 27, in combination with the support 26, isolates the electrodes 21, 22, 23 and 24 and the extensions 23b and 24b from outside and protect them against water penetration from outside.

Urine guides 28 which partially expose the pair of urine sensor electrodes 21 and 22 and guide urine are formed in the covering 27. A plurality of such urine guides 28 are arranged symmetrically with respect to the longitudinal center line of the support 26 at the ends of the urine sensor electrodes 21 and 22 and their vicinities. As shown in FIG. 4, when adhesion of urine A occurs across between the urine guides 28 above the pair of urine sensor electrodes 21 and 22, short-circuiting occurs between the electrodes 21 and 22, so excretion of urine A is detected. The urine sensor electrodes 21 and 22 are hereinafter referred to as a urine sensor.

Also, feces guides 29 which partially expose the pair of feces sensor electrodes 23 and 24 and guide feces are formed in the covering 27. One left feces guide 29 and one right one 29 are arranged symmetrically with respect to the longitudinal center line of the support 26 in the extensions 23b and 24b of the feces sensor electrodes 23 and 24. As shown in FIG. 5, when adhesion of feces B occurs across between the feces guides 29 above the pair of feces sensor electrodes 23 and 24, short-circuiting occurs between the electrodes 23 and 24, so adhesion of feces B is detected. The feces sensor electrodes 23 and 24 are hereinafter referred to as a feces sensor.

In the support 26 and covering 27, a plurality of urine passage holes 25 are formed in a way to penetrate between their front and back surfaces. The excreted urine passes through a urine passage hole 25 and the back side of the support 26 before being received by the urine tray 13.

As shown in FIG. 1, the apparatus body 2 includes: a urine tank 51 to which one end of a urine guide tube 30 is connected; a vacuum pump 52 connected with the urine tank 51; a control unit 53 which controls the vacuum pump 52, switch circuit 56, and polarity reversal circuit 57; a DC power supply 54 which applies voltage between the electrodes 21 and 22 or 23 and 24 of the excretion sensor 10 through electric wires 61 or 62; a detection means 55 which detects output (resistance) of the excretion sensor 10; a switch circuit 56 which turns on and off the electric wires 61 and 62 to the electrodes 21, 22, 23 and 24 of the excretion sensor 10; and a polarity reversal circuit 57 which reverses the polarity of the electric wires 61 and 62 to the electrodes 21, 22, 23 and 24 of the excretion sensor 10. The DC power supply 54 is, for example, an AC adapter or battery.

The control unit 53 is supplied with electric power from the DC power supply 54 through electric wires 64 and controls the vacuum pump 52, switch circuit 56 and polarity reversal circuit 57. The control unit 53 incorporates a timer.

The control unit 53 controls the vacuum pump 52 according to the result of detection of the resistance between the pair of urine sensor electrodes 21 and 22 by the detection means 55. Specifically, when short-circuiting occurs between the electrodes 21 and 22 and the control unit 53 detects a drop in the electric resistance between the electrodes 21 and 22 to a prescribed level or less through the detection means 55, the control unit 53 determines that urination has occurred and starts the vacuum pump 52. As the vacuum pump 52 is started, the amount of urine in the excretion receiver 1 decreases and the control unit 53 detects a rise in the electric resistance between the electrodes 21 and 22 to a prescribed level or more through the detection means 55; then it starts the timer and continues to run the vacuum pump 52. As this timer reaches a prescribed time, the control unit 52 stops running the vacuum pump 52.

In addition, the control unit 53 activates a warning device (not shown) according to the result of detection of the resistance between the pair of feces sensor electrodes 23 and 24 by the detection means 55. Specifically, when short-circuiting occurs between the electrodes 23 and 24 and the control unit 53 detects a drop in the electric resistance between the electrodes 23 and 24 to a prescribed level or less through the detection means 55, the control unit 53 determines that defecation has occurred and activates the warning device to give an alarm.

The vacuum pump 52 is supplied with electric power from the DC power supply 54 through electric wires 63 and sucks in the air in the urine tank 51 to suck out the urine received by the excretion receiver 1 through the urine guide tube 30 and store it in the urine tank 51.

A connector 42 is provided at the ends of the electric wires 61 and 62. This connector 42 is detachably coupled with the base end of the excretion sensor 20. When the connector 42 is coupled with the base end of the excretion sensor 20, the terminals 21a and 22a are electrically connected with the electric wires 61 and also the terminals 23a and 24a are electrically connected with the electric wires 62.

As shown in FIG. 6, the switch circuit 56 includes switches 56a which turn on and off the electric wires 61 to the electrodes 21 and 22, and switches 56b which turn on and off the electric wires 62 to the electrodes 23 and 24. In other words, the switch circuit 56 includes switches 56a which turn on and off the urine sensor and switches 56b which turn on and off the feces sensor. FIG. 6 is a diagram which schematically shows the electrical system of the excretion sensor 20 shown in FIG. 1.

The polarity reversal circuit 57 includes a polarity reversal circuit 57a which reverses the polarity of the electric wires 61 to the electrodes 21 and 22, and a polarity reversal circuit 57b which reverses the polarity of the electric wires 62 to the electrodes 23 and 24. In other words, the polarity reversal circuit 57 includes a polarity reversal circuit 57a which reverses the polarity of the urine sensor, and a polarity reversal circuit 57b which reverses the polarity of the feces sensor.

Next, control operation of the excrement treating apparatus 100 will be described referring to FIG. 1 and FIGS. 6 to 8. FIG. 7 is a diagram which shows state change of the electrical system of the excretion sensor 20 as shown in FIG. 6. FIG. 8 is a time chart which shows change in voltage depending on the state change as shown in FIG. 7.

When a wearer of the excretion receiver 1 excretes urine and adhesion of urine A occurs across between the urine guides 28 above the urine sensor electrodes 21 and 22, short-circuiting occurs between the electrodes 21 and 22 and the detection means 55 thus detects excretion of the urine A. According to a urine detection signal from the detection means 55, the control unit 53 starts the vacuum pump 52 to begin suction of urine from the excretion receiver 1 through the urine guide tube 30 and also starts the built-in timer.

In impurities contained in the urine excreted by the person, there is a substance which is attracted to the positive pole and/or negative pole of the electrode 21 or 22 and accumulates on its conductive surface and interferes with electrical conduction between the electrodes 21 and 22, so if the polarity of the electrodes 21 and 22 is always the same, the interfering substance would be continuously attracted to the positive pole and/or negative pole and accumulated during operation of the excretion sensor 20.

This means that impurities in urine accumulate on the conductive surface of the electrode and the urine sensor becomes less sensitive and fails to detect urination immediately. A major reason for this is that in the impurities contained in the urine excreted by a person there is a substance which is attracted to an electrode of the excretion sensor and accumulates on its conductive surface and interferes with electrical conduction between electrodes (for example, an organic substance such as a protein or inorganic ions), and when voltage is applied to the urine sensor's electrodes for detection, depending on the electrical polarity of such interfering substance, positively charged interfering substance is attracted to the negative pole (minus pole) and a negatively charged interfering substance is attracted to the positive pole (plus pole) and accumulates thereon.

In this embodiment, the control unit 52 always activates the polarity reversal circuit 57a at prescribed time intervals during operation of the excretion sensor 20 to reverse the polarity of the electric wires 61 in order to reverse the polarity of the electrodes 21 and 22. Consequently, the interfering substance accumulated on each pole is repelled by reversing the pole polarity from positive to negative or vice versa, or it is discharged together with the urine sucked into the urine guide tube 30 by eliminating the attracting force. By continuously reversing the polarity of the electrodes at prescribed time intervals, the conductive surfaces of the electrodes 21 and 22 are always refreshed and the sensitivity of the excretion sensor 20 is thus stabilized, so urination can be accurately detected and treated.

The control unit 52 controls so as to apply voltage between the urine sensor electrodes 21 and 22 intermittently. Consequently, when urination is detected by the urine sensor electrodes 21 and 22, there is periodically a time zone in which no voltage is applied, and in such a time zone in which no voltage is applied, the interfering substance is discharged together with the urine and the sensitivity of the excretion sensor 20 is thus stabilized, so urination can be accurately detected and treated.

During its operation, the control unit 52 controls so as to perform switching between a state where switches 56a are On and switches 56b are Off (FIG. 7(a) or 7(c)) and a state where switches 56a are Off and switches 56b are On (FIG. 7(b) or 7(d)) at prescribed time intervals. In other words, the control unit 52 controls so that when the switches 56a are On, the switches 56b are Off, and when the switches 56a are Off, the switches 56b are On.

Consequently, even if excreted urine enters both the urine guides 28 and the feces guides 29 and adheres to them, during time zones for urine detection, $t_1$ and $t_3$, only short-circuiting between the urine guides 28 is detected, so urination can be detected in a way to be distinguished from defecation. Conversely, even if excreted feces enters both the feces guides 29 and the urine guides 28 and adheres to them, during time zones for feces detection, $t_2$ and $t_4$, only short-circuiting between the feces guides 29 is detected, so defecation can be detected in a way to be distinguished from urination. Therefore, it cannot happen that urination and defecation are detected wrongly and the vacuum pump 52 is activated upon defecation or a warning device is activated upon urination; as a consequence, the excrement treating apparatus 100 can be user-friendly.

As suggested by the order of (a), (b), (c), and (d) in FIG. 7 and the order of $t_1$, $t_2$, $t_3$ and $t_4$ in FIG. 8, the control unit 53 controls so as to perform alternately switching between urine detection by the urine sensor electrodes 21 and 22 and feces detection by the feces sensor electrodes 23 and 24 and switching between polarity reversal of the urine sensor electrodes 21 and 22 and polarity reversal of the feces sensor electrodes 23 and 24. This makes the sensitivity of the excretion sensor 20 more stable.

Here, prescribed time intervals $t_1+t_2$ and $t_3+t_4$ for polarity reversal of the urine sensor electrodes 21 and 22 and the feces sensor electrodes 23 and 24 are not more than 1 second and not less than 0.1 second. For the purpose of stabilizing the urine detection sensitivity, it is preferable that the prescribed time intervals $t_1+t_2$ and $t_3+t_4$ be short and when two sensor lines are used for urine and feces, it is also desirable to make the prescribed time intervals $t_1+t_2$ and $t_3+t_4$ short in order to minimize delay in detection, because while one sensor line is active, the other sensor line is inactive. However, if the prescribed time intervals $t_1+t_2$ and $t_3+t_4$ are too short, the circuitry for polarity reversal and detection must be complicated and expensive, so the optimum range for the prescribed time intervals $t_1+t_2$ and $t_3+t_4$ is from 0.1 to 1 second.

Although all the time zones in the prescribed time intervals are the same time periods in this embodiment, they may be different time periods.

The voltage applied between the urine sensor electrodes 21 and 22 and between the feces sensor electrodes 23 and 24 is within the range from 1 to 10 V. If this voltage is too low, the susceptibility to an interfering substance would be increased and it has been found that when the voltage is 1 V or more and the polarities of the urine sensor electrodes 21 and 22 and feces sensor electrodes 23 and 24 are reversed at prescribed time intervals, the detection sensitivity (apparent electric resistance) is particularly stable. However, since the excretion receiver 1 is to be worn on the human body, for safety reasons the voltage should not be too high and it is most appropriate to set the voltage within the range from 1 to 10 V.

Description Of Reference Numerals

Figure 1:
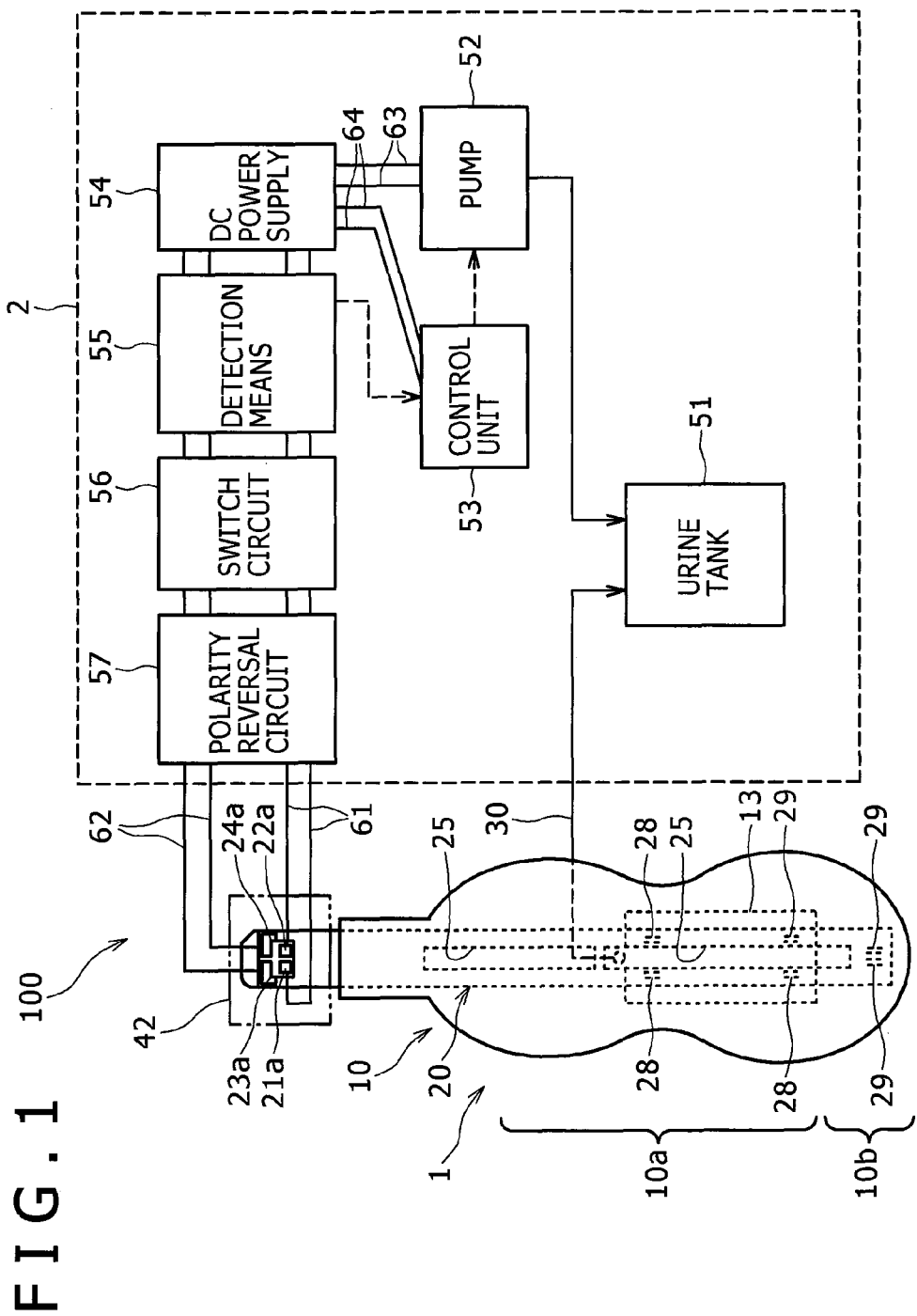
[FIG. 1] is a block diagram of an excrement treating apparatus according to an embodiment of the present invention.
Figure 2:
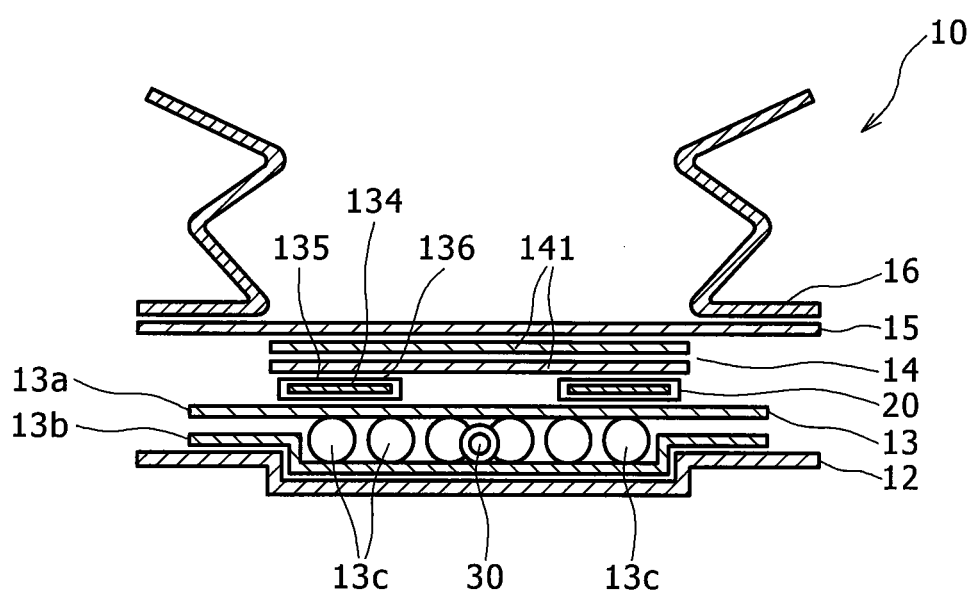
[FIG. 2] is an enlarged sectional view of an excretion receiver shown in FIG. 1.
Figure 3:
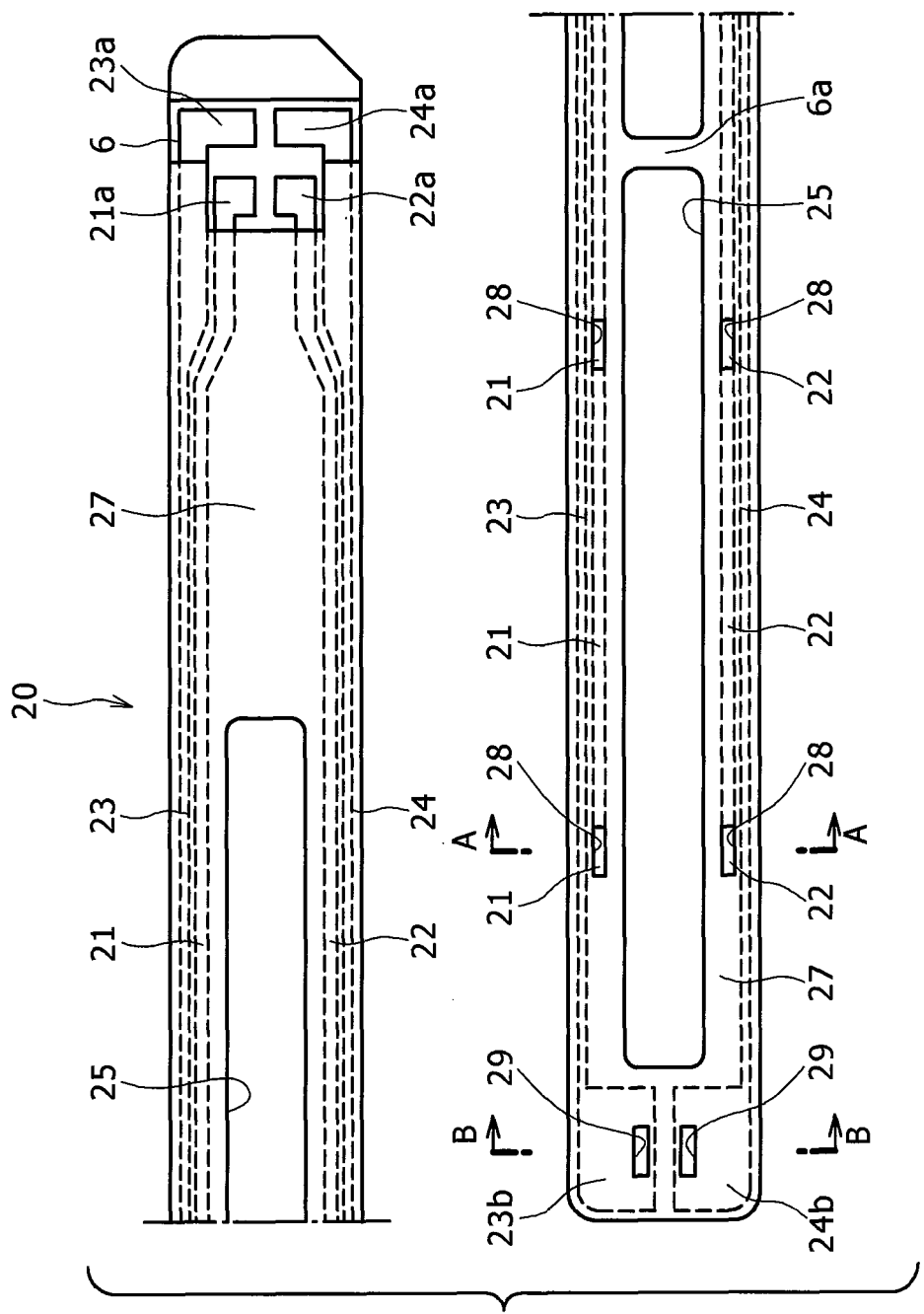
[FIG. 3] is a plan view of an excretion sensor shown in FIG. 1 which is divided in halves in the illustration.
Figure 4:
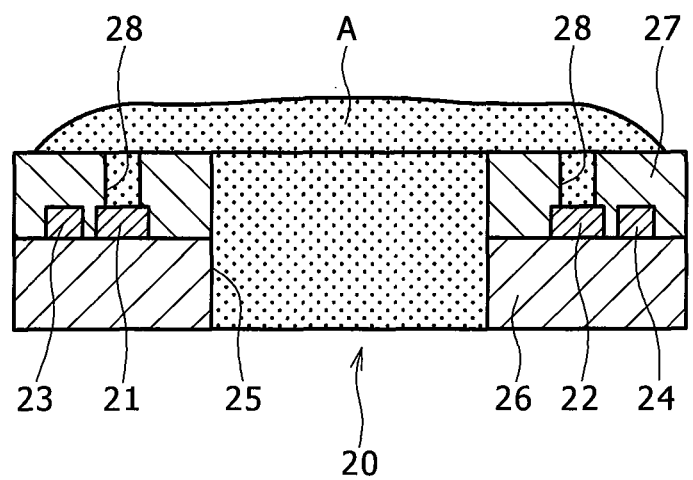
[FIG. 4] is a sectional view taken along the line A-A in FIG. 3.
Figure 5:
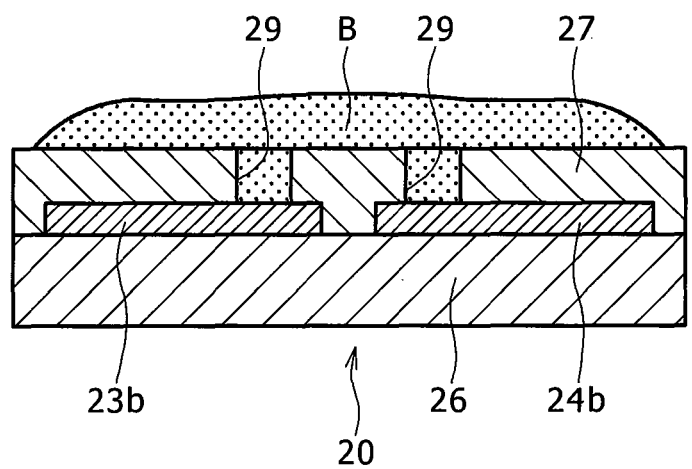
[FIG. 5] is a sectional view taken along the line B-B in FIG. 3.
Figure 6:
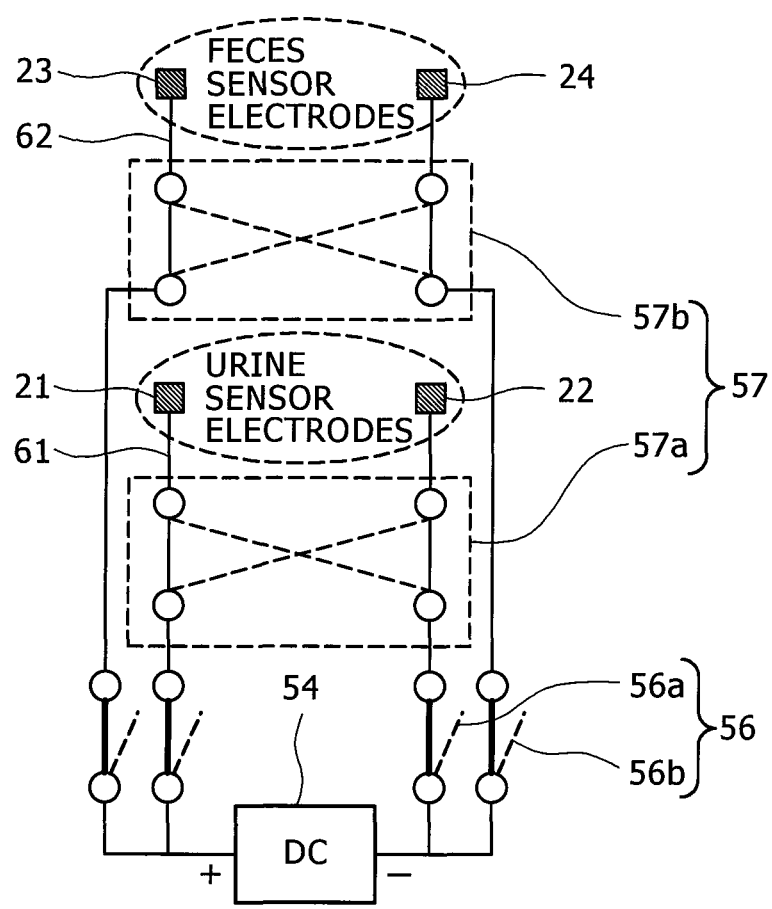
[FIG. 6] is a diagram which schematically shows the electrical system of the excretion sensor shown in FIG. 1.
Figure 7:
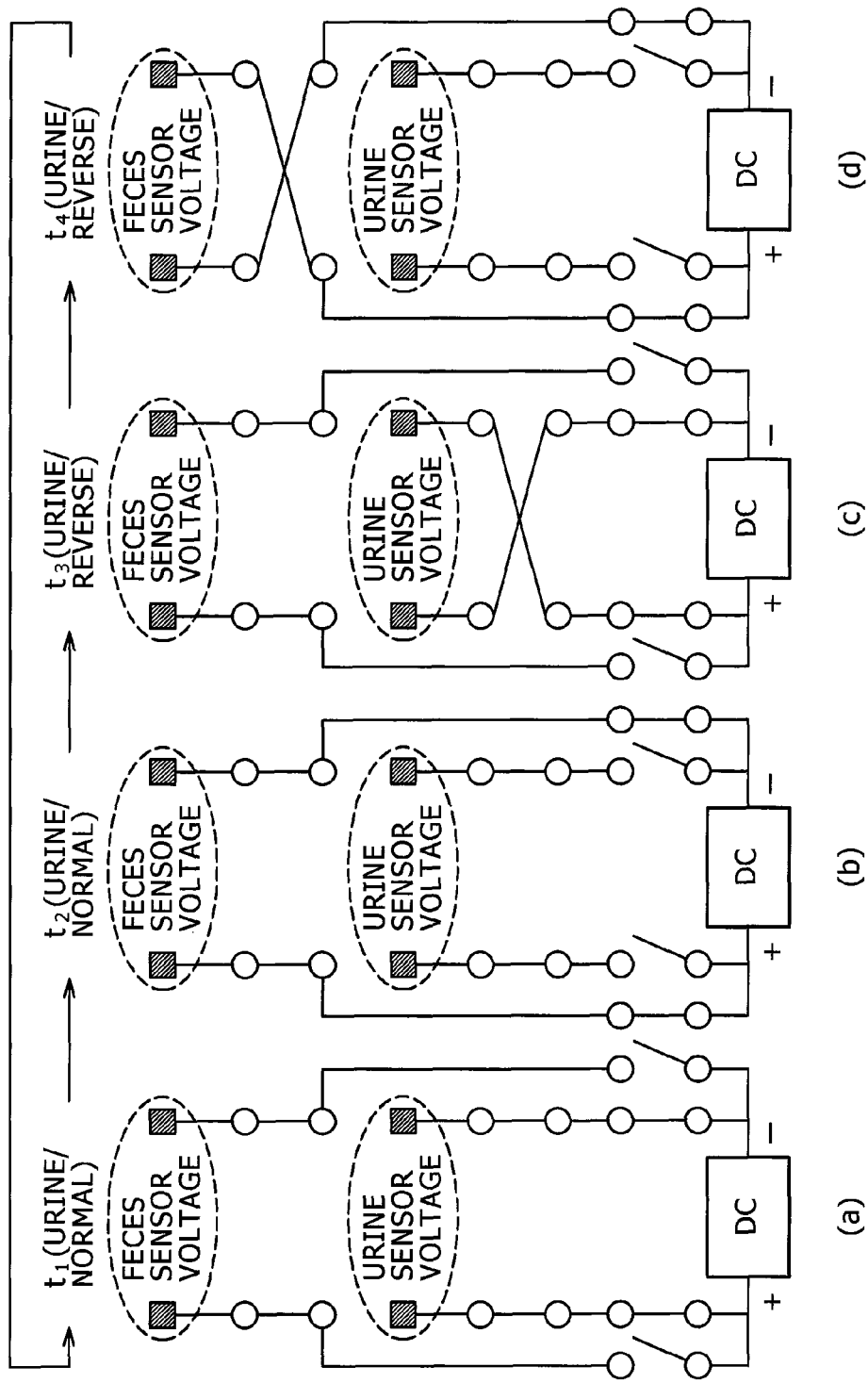
[FIG. 7] is a diagram which shows state change of the excretion sensor's electrical system shown in FIG. 6.
Figure 8:
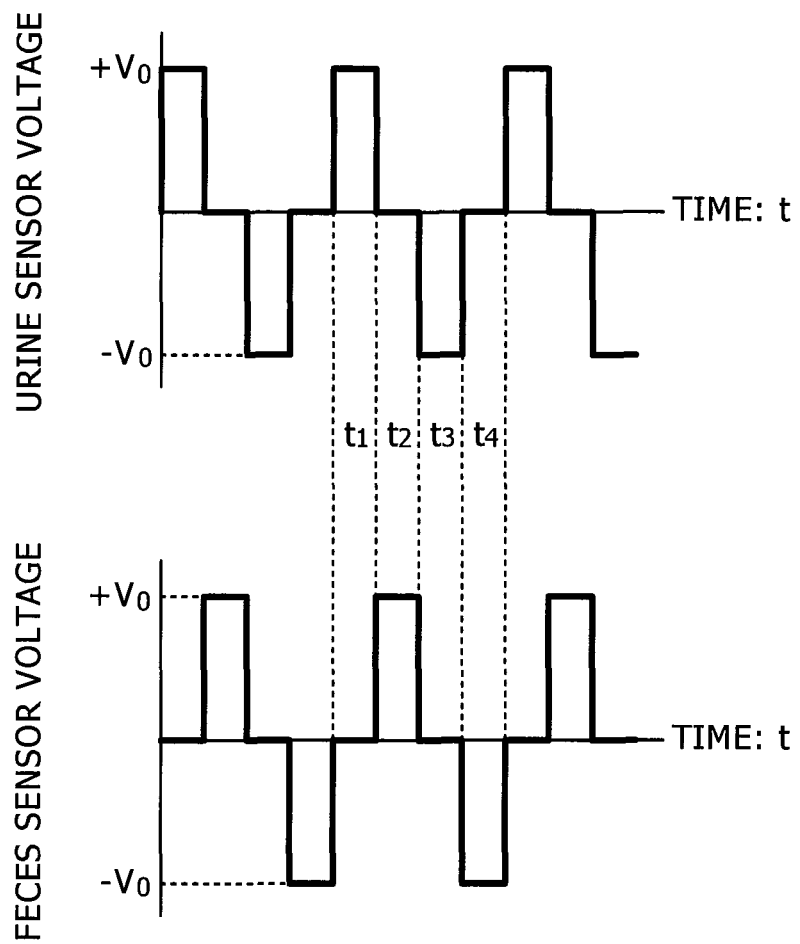
[FIG. 8] is a time chart which shows voltage change depending on the state change shown in FIG. 7.

1 . . . Excretion receiver
2 . . . Apparatus body
10 . . . Receiver body
10a . . . Urine receiving portion
10b . . . Feces receiving portion
12 . . . Back sheet
13 . . . Urine tray
14 . . . Surface material member
15 . . . Surface sheet
16 . . . Gathering
20 . . . Excretion sensor
21, 22, 23, 24 . . . Electrodes
21a, 22a, 23a, 24a . . . Terminals
23b, 24b . . . Extensions
25 . . . Urine passage hole
26 . . . Support
27 . . . Covering
28 . . . Urine guides
29 . . . Feces guides
30 . . . Urine guide tube
42 . . . Connector
51 . . . Urine tank
52 . . . Vacuum pump
53 . . . Control unit
54 . . . DC power supply
55 . . . Detection means
56 . . . Switch circuit
57 . . . Polarity reversal circuit
61-64 . . . Electric wires
100 . . . Excrement treating apparatus

The invention claimed is:
1. An excrement treating apparatus comprising:
an excretion receiver to be worn by a person; and
an apparatus body detachably connected with the excretion receiver;
the excretion receiver including:
   a receiver body which receives excretions discharged from a wearer; and
   an excretion sensor which detects the excretions;
the apparatus body including:
   a urine tank which stores urine;
   a vacuum pump which sucks in the air in the urine tank to suck out the urine received by the receiver body into the urine tank;
   a DC power supply;
   a switch circuit;
   a polarity reversal circuit; and
   a control unit which controls the vacuum pump, the switch circuit and the polarity reversal circuit,
the excretion sensor including:
   one pair of urine sensor electrodes which detect urine received by the receiver body and are one of two pairs of electrodes extending in parallel along the receiver body and urine guides partially exposing the urine sensor electrodes formed into the receiver body; and
   one pair of feces sensor electrodes which detect feces received by the receiver body and are another one of the two pairs of electrodes and feces guides partially exposing the feces sensor electrodes formed into the receiver body,
wherein the DC power supply applies voltage between the urine sensor electrodes and applies voltage between the feces sensor electrodes;
the switch circuit turns on and off electric wires to the urine sensor electrodes and the feces sensor electrodes;
the polarity reversal circuit reverses the polarity of the electric wires to the urine sensor electrodes;
the control unit performs:
   switching between urine detection by the urine sensor electrodes and feces detection by the feces sensor electrodes at prescribed time intervals;
   reversing the polarity of the electric wires to the urine sensor electrodes at prescribed time intervals; and
urine detection according to the result of detection of electric resistance between the urine sensor electrodes and feces detection according to the result of detection of electric resistance between the feces sensor electrodes.

2. The excrement treating apparatus according to claim 1, wherein the apparatus body includes a connector connected with electric wires extending from the DC power supply,
and the urine sensor electrodes and the feces sensor electrodes are connected with the DC power supply through the connector and the electric wires.

3. The excrement treatment apparatus according to claim 1, wherein the excretion sensor has a plurality of urine guides and a plurality of feces guides arranged alternately.

\* \* \* \* \*